United States Patent [19]
Rise

[11] Patent Number: 5,421,809
[45] Date of Patent: Jun. 6, 1995

[54] BACK SUPPORT BELT

[76] Inventor: Mark J. Rise, 700 Bales Rd., Apt. 26, McAllen, Tex. 78503

[21] Appl. No.: 113,915

[22] Filed: Aug. 13, 1993

Related U.S. Application Data

[63] Continuation of Ser. No. 841,425, Feb. 26, 1992, abandoned.

[51] Int. Cl.⁶ .................................................. A61F 5/02
[52] U.S. Cl. ............................................. 602/19; 2/44; 128/876
[58] Field of Search ................. 128/99.1–112.1, 128/116.1, 95.1, 96.1, 78, 870, 871, 874, 875, 876, 160, 161, 169; 607/112, 108; 602/19, 20, 23, 60, 61; 2/44

[56] References Cited

U.S. PATENT DOCUMENTS

| | | | |
|---|---|---|---|
| 1,052,523 | 2/1913 | Sillin | 128/96.1 |
| 3,096,760 | 7/1963 | Nelkin . | |
| 3,141,457 | 7/1964 | Davidson | 128/95.1 |
| 3,927,665 | 12/1975 | Wax . | |
| 4,022,197 | 5/1977 | Castiglia | 128/96.1 |
| 4,135,503 | 1/1979 | Romano . | |
| 4,475,543 | 10/1984 | Brooks et al. . | |
| 4,552,135 | 11/1985 | Racz et al. . | |
| 4,572,167 | 2/1986 | Brunswick | 2/44 |
| 4,768,499 | 9/1988 | Kemp . | |
| 4,802,667 | 2/1989 | Altner . | |
| 4,833,730 | 5/1989 | Nelson | 2/44 |
| 4,845,911 | 5/1988 | Bender . | |
| 4,905,993 | 3/1990 | Barone . | |
| 4,907,576 | 3/1990 | Curlee | 602/19 |
| 4,964,401 | 10/1990 | Taigen | 128/876 |
| 4,968,027 | 11/1990 | Anderson . | |
| 4,991,573 | 2/1991 | Miller | 128/106.1 |
| 5,029,341 | 7/1991 | Wingo | 2/44 |
| 5,046,488 | 9/1991 | Schiek, Sr. | 2/44 |
| 5,062,414 | 11/1991 | Grim | 128/384 |
| 5,070,866 | 12/1991 | Alexander | 128/876 |
| 5,086,758 | 2/1992 | Schick, Sr. | 128/876 |
| 5,179,942 | 1/1993 | Drulias | 128/101.1 |
| 5,207,635 | 5/1993 | Richards | 128/876 |

Primary Examiner—Mickey Yu
Assistant Examiner—David J. Kenealy
Attorney, Agent, or Firm—Gregory W. Carr

[57] ABSTRACT

The invention includes a back support belt having a dual-belt assembly in which a wide, elastic inner belt completely encircles the abdominal and lower lumbar regions of the body. The inner belt is secured before a second, relatively less elastic outer belt, primarily providing rigid support, is fastened over the inner belt. The middle and side panels of the inner belt provide additional support to critical areas of the region through the use of supplemental internal padding.

12 Claims, 5 Drawing Sheets

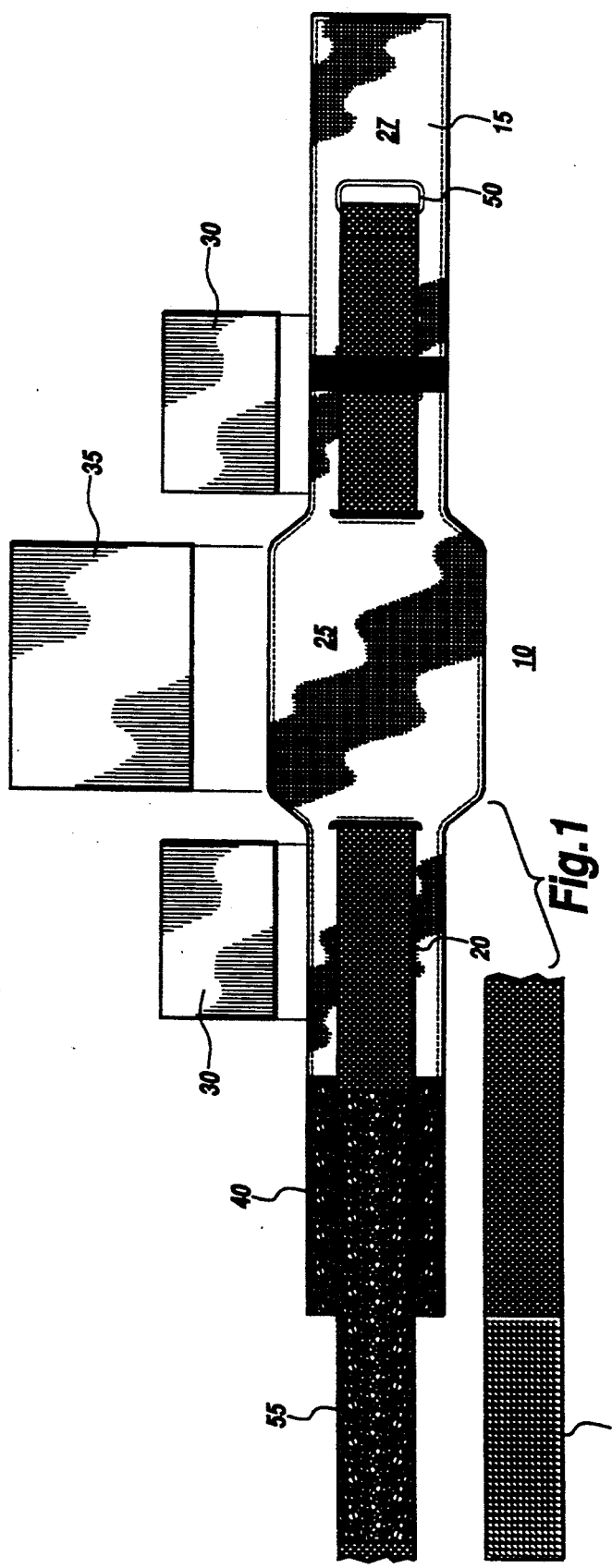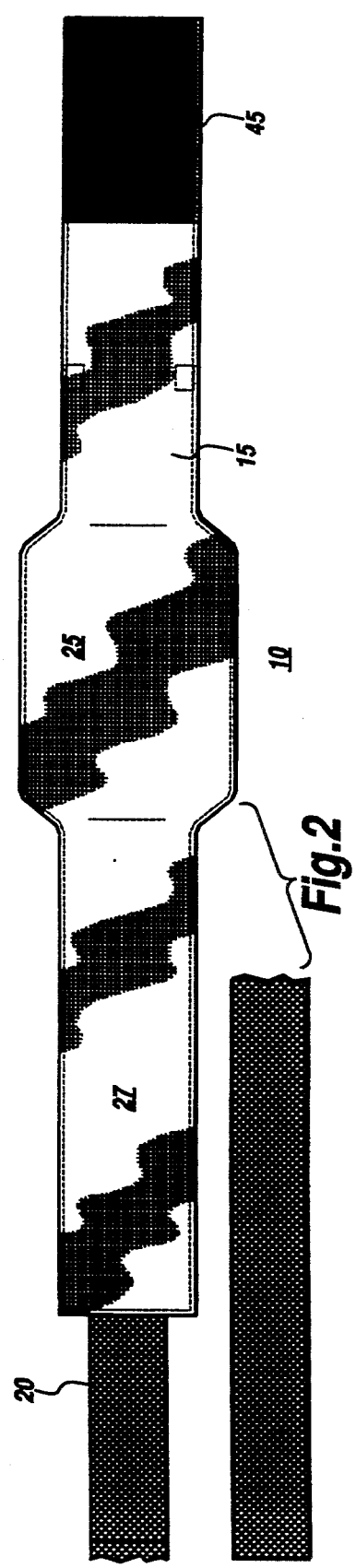

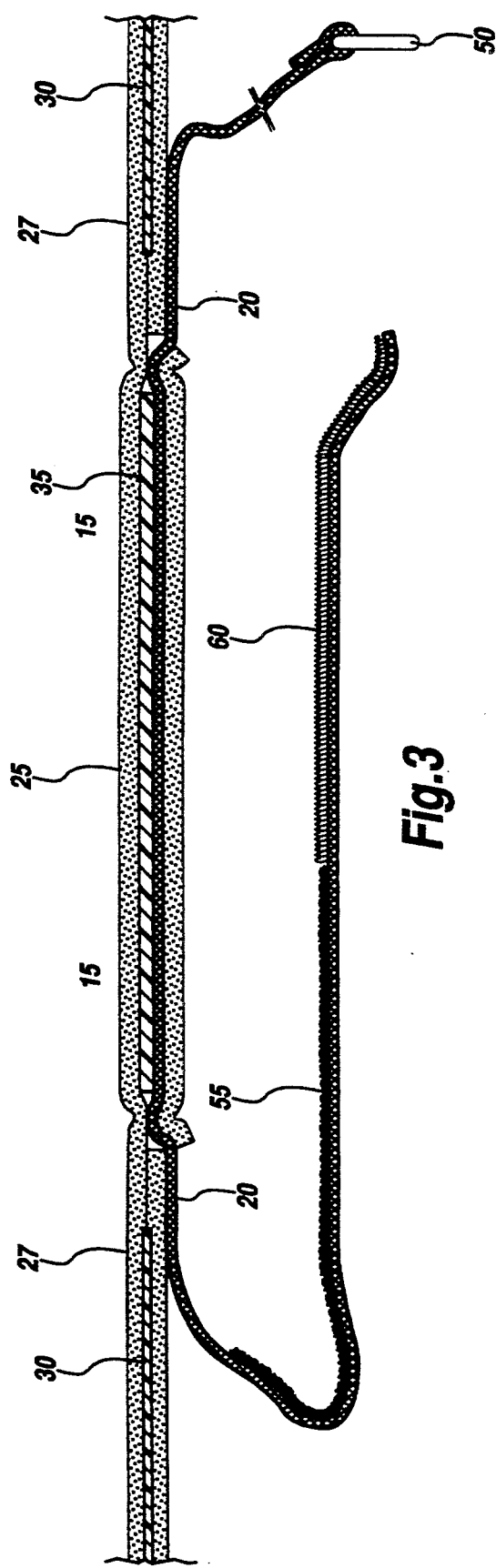

BACK SUPPORT BELT

CONTINUING DATA

This case is a continuation of Ser. No. 07/841,425, Feb. 26, 1992, which is now abandoned.

TECHNICAL FIELD

This invention relates to support devices for individuals and, more particularly, to a support belt for supporting and protecting the lumbar and abdominal regions of the body during strenuous activities.

BACKGROUND AND SUMMARY

The spine and spinal column are extremely complex and delicate components of the human skeletal system. Made up of thirty-three bones, cartilage, ligaments and several major and minor muscles groups, these components are primarily responsible for support and protection of the body. An injury or strain to the lower back region of the body can result in excruciating pain and complete or partial loss of mobility. Moreover, lower back strain or injury can often persist long after the initial injury, producing years of pain and discomfort. Finally, back strain and injury, while comprising a significant number of activity-related injuries in the United States, remains one of the most difficult areas of diagnosis and treatment for the medical community.

To reduce the probability of injury to this region of the body, many back support devices have been developed over the years. A number of these devices have been designed to protect the lower lumbar region of the body for a particular type of activity. However, these types of support belts are either too flexible or too rigid to provide adequate support for a variety of user activities. For instance, a leather weight belt provides rigid support for the weight lifter, but is too inflexible to provide comfortable support during other more dynamic activities.

Other types of support belts have been developed to aid in the rehabilitative treatment of back injuries once injury has occurred. While providing adequate treatment alternatives once an injury is present, these belts do not offer the support and protection necessary to prevent injury to the region. Still other belts have been developed more to provide proper placement of various devices adjacent to the lower lumbar region of the body than to provide support or protection for the region. Moreover, many of the existing back support devices are complicated to use and do not offer a comfortable, correct fit.

The present invention provides a solution to the aforementioned shortcomings of available back supports. The invention is a back support belt having a dual-belt construction in which a wide, relatively elastic inner belt completely encircles the abdominal and lower back regions of the body and is secured prior to the fastening of a second, relatively less elastic outer belt. The elastic inner belt primarily provides a correct and comfortable fit while the relatively less elastic outer belt provides the rigid support needed to adequately protect the body region. The middle panel of the elastic inner belt contains additional internal padding which provides increased protection for the vulnerable central lumbar area of the lower back. The side panels of the inner belt contain foam rubber padding which supports the oblique muscles of the body in a comfortable manner during use. The differing elastic properties of the two belts provide both comfort and support simultaneously.

Muscle groups located in both the lower back and the abdomen play a role in the exertion of force through lifting, pushing or pulling activities. An additional feature of the belt is that it is substantially uniform in width and thickness throughout its length. This feature not only provides direct support to the lower back region of the body, it also allows the abdominal muscle groups to push against the support belt, thus increasing the intra-abdominal pressure and indirectly reducing stress on the spine and lower back. Thus the support belt strengthens the entire body region in a manner superior to support devices only providing support to the lower back region of the body.

In operation, the support belt is fastened around the body in a few, simple steps. First, the support belt is placed around the waist of the user. Next the inner, relatively elastic belt is closed around the user and secured. The fasteners are shaped and located such that the inner belt can be comfortably and correctly fit to users of all sizes. Finally, the outer, relatively less elastic belt, which is longer than the inner belt, is closed around the inner belt and secured by a ring and Velcro® fasteners. The combination of an elastic inner belt and a relatively less elastic outer belt provides a comfortable, protective support belt which is also quick and simple to use.

BRIEF DESCRIPTION OF THE DRAWINGS

A more complete understanding of the invention may be had by reference to the following Detailed Description when taken in conjunction with the accompanying Drawings in which:

FIG. 1 is a plan view, showing the front of the invention in a flat condition and the supplemental support padding found within the rear middle panel and side panels exploded away from the body of the invention;

FIG. 2 is a plan view, showing the rear of the invention in a flat condition;

FIG. 3 is a cross section of the invention disposed in a flat condition, illustrating the supplemental padding of the side and middle panels of the inner belt of the invention;

DETAILED DESCRIPTION

Figure 4:
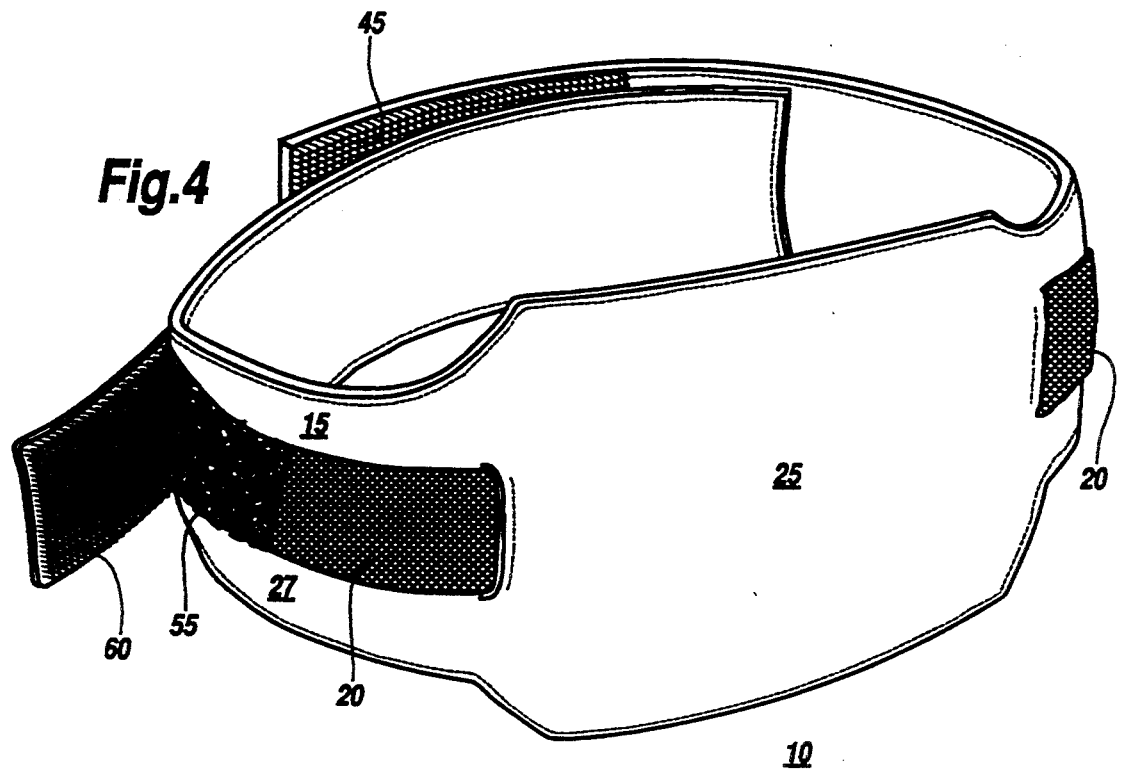
FIG. 4 is a perspective view, showing from the rear the invention fastened.

A support belt 10 incorporating the present invention is shown in FIG. 1. The support belt 10 comprises a dual-belt assembly in which a wide inner belt 15 and an outer belt 20 completely encircle the abdominal and lower lumbar regions of the body. The inner belt 15 is fastened independently of the outer belt 20. The inner belt 15 is wider and shorter than the outer belt 20 and has a relatively wider middle panel 25 for increased support of the lower lumbar region of the back. Additionally, the side panels 27 of the inner belt 15 contain supplemental padding for increased support of the oblique muscles during use. As best illustrated in FIG. 3, the inner belt 15 is comprised of two sheets of an elastic, durable material stitched around soft flexible padding 30 along its side panels 27 and a more rigid pad 35 located in the middle panel 25 of the inner belt 15. The inner belt 15 primarily provides a correct and comfortable fit of the support belt 10 on the individual. Although the inner belt 15 shown is constructed of neoprene and foam rubber, it will be appreciated that other suitable materials may be used, if desired.

The outer belt 20, relatively less wide and longer than the inner belt 15, overlies the inner belt 15 of the support belt 20. Once the inner belt 15 is fastened, the outer belt 20 is placed around the inner belt 15 and secured. The outer belt 20 is attached to the inner belt 15 at only two points along their lengths. As the outer belt 20 passes into, is layered with, and emerges out of the middle panel 25 of the inner belt 15, it is stitched on either side of the middle panel 25 to the inner belt 15. Being attached at only these two points allows the inner belt 15 and outer belt 20 to perform independently of each other. The outer belt 20 is comprised of a relatively less elastic, durable material and primarily provides support to the body region. Although the outer belt 20 shown is constructed of woven nylon webbing, it will be appreciated that other suitable materials may be used, if desired.

Referring again to FIG. 1, a square strip of Velcro ® (loops) fastener 40 and a larger rectangle of Velcro ® (hooks) fastener 45 located at the opposite ends of the inner belt 15 of the support belt 10 provide the fastening means for securing the inner belt 15 around the body. A metallic ring 50 at one end and a Velcro ® strip (loops) fastener 55 and Velcro ® strip (hooks) fastener 60 at the opposite end of the outer belt 20 provide the fastening means for securing the outer belt 20 around the inner belt 15 of the support belt 10. Although the fastening means for the support belt 10 include the use of a combination of Velcro ® fasteners and the metallic ring 50, it will be appreciated that other suitable means of fastening may be utilized, if desired.

Figure 5:
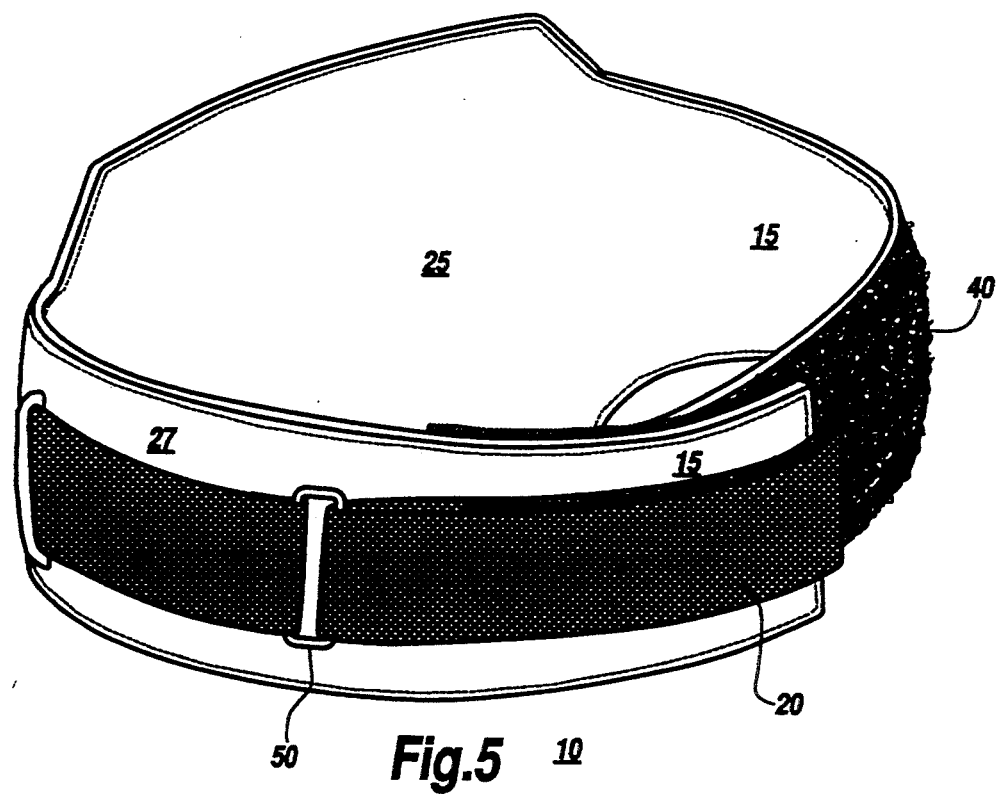
FIG. 5 is a perspective view, showing from the front the invention fastened.
Figure 6:
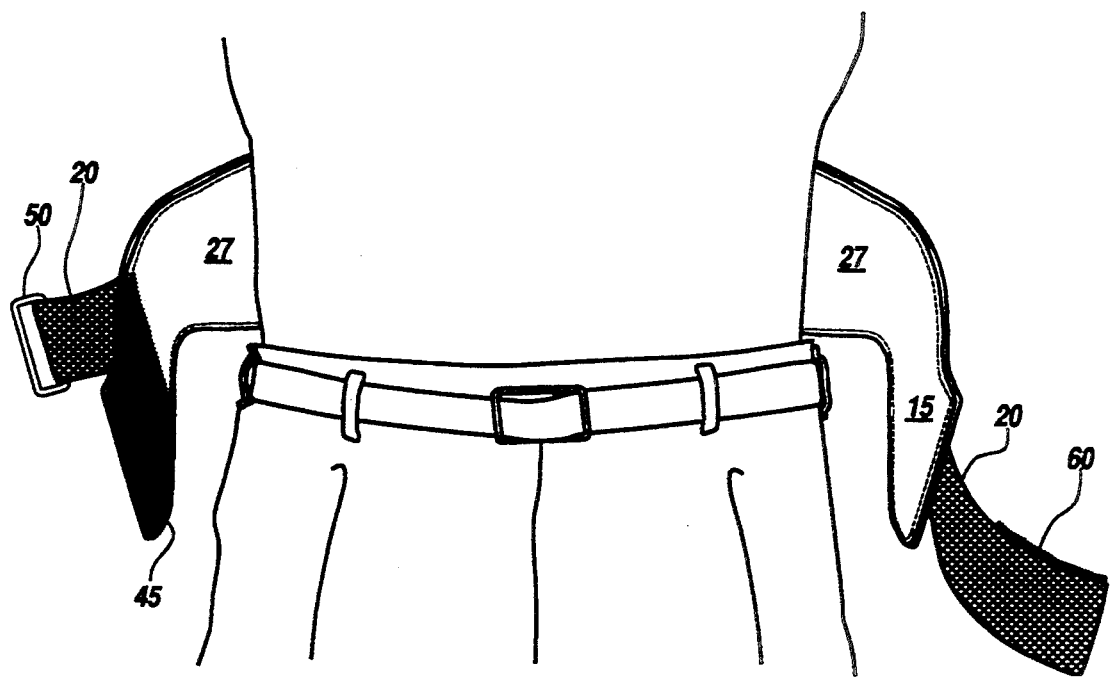
FIGS. 6 through 9 are front perspective views and demonstrate the series of steps involved with placement and engagement of the invention on an individual.
Figure 7:
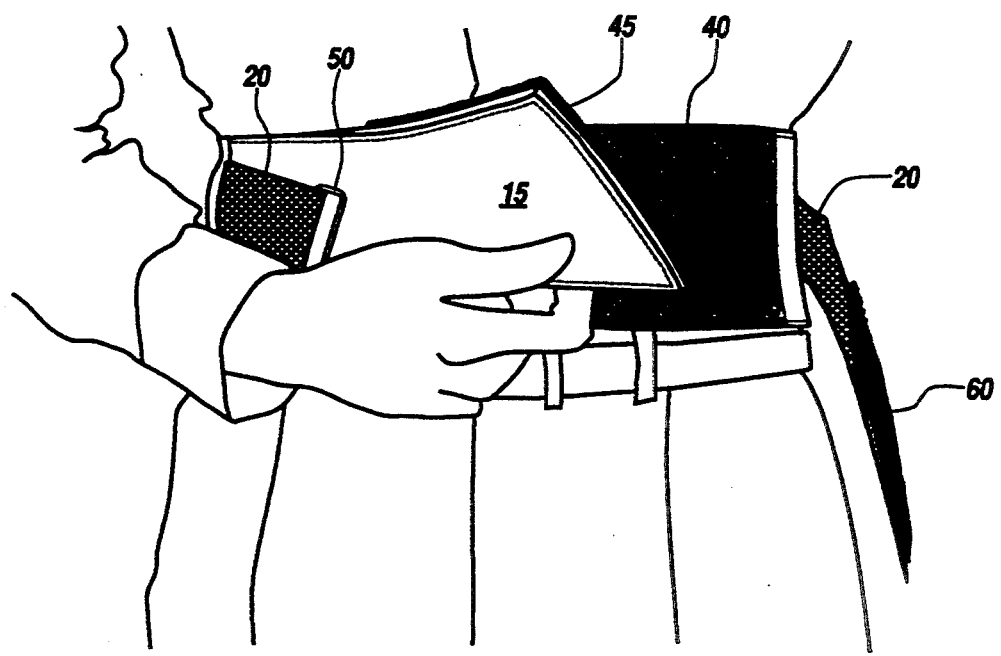
Figure 8:
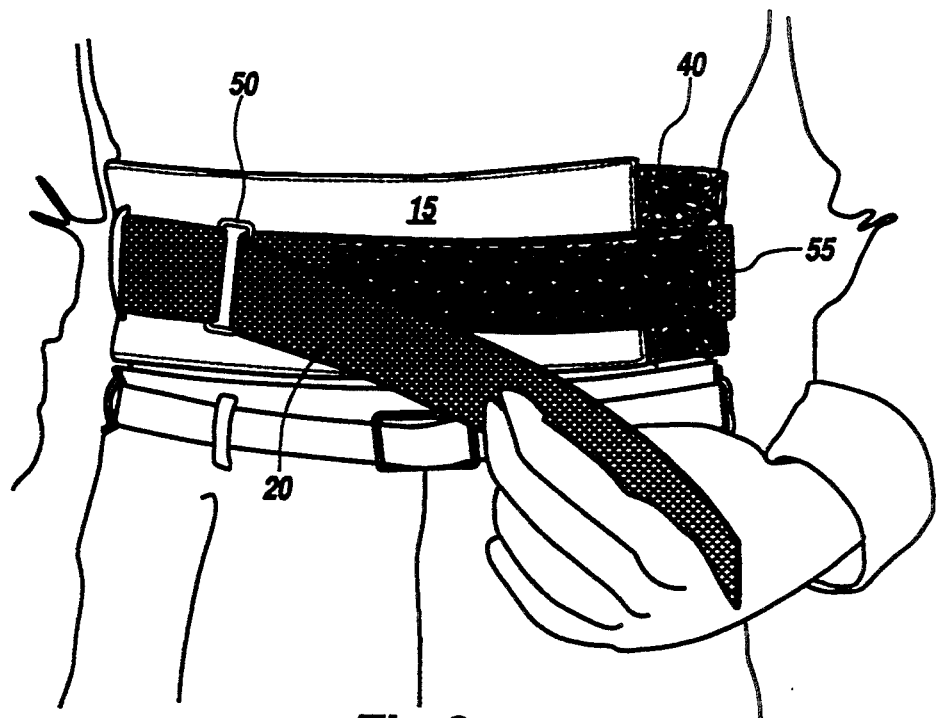
Figure 9:
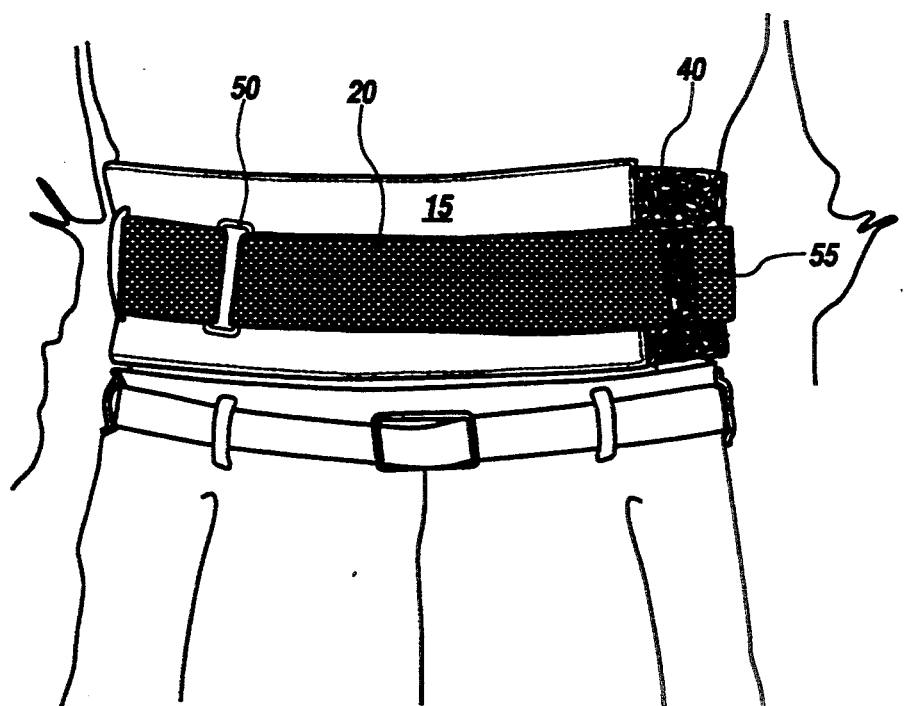

FIGS. 5, 6 and 7 demonstrate the series of steps associated with proper placement and fastening of the support belt 10. In FIG. 5, the support belt 10 is placed around the waist of the body with the wide, elastic inner belt 15 positioned next to the body. FIG. 6 demonstrates the user stretching the belt around the waist and engaging and securing the Velcro ® fasteners 40 and 45 of the inner belt 15. As previously discussed, the location and design of the fasteners 40 and 45 allows the support belt 10 to be fit correctly and comfortably to individuals of all sizes. Once the inner belt 15 is secured, the outer belt 20 is fastened over the inner belt 15 by passing the free end of the outer belt 20 through the metallic ring 50 on the opposite end of the outer belt 20, reversing directions and cinching it tightly as illustrated in FIG. 7. The outer belt 20 is further secured by engaging and securing the Velcro ® fasteners 55 and 60 located at the free end of the outer belt 20. This fastening sequence allows the support belt 10 to be fitted to different size users, and facilitates quick and easy attachment and removal of the support belt 10.

Once in place, the relatively uniform width and thickness of the inner belt 15 and the support of the relatively less elastic outer belt 20 function in concert to provide support to both the lower lumbar and abdominal regions of the body. Importantly, the uniform width and thickness of the support belt 10 provides both direct and indirect support to the lower back region. Direct support is primarily provided through the wide middle panel 25 of the inner belt 15. Indirect support for the lower back is achieved by providing support to the abdominal region of the body. The abdominal muscles push against the wide, inner belt 15 of the support belt 10 during strenuous activity, thus increasing the amount of intra-abdominal pressure and indirectly providing support to the lower back and spine. Therefore the design of the support belt 10 provides both a comfortable and correct fit as well as direct and indirect support to the body region in a manner superior to existing back support devices.

Only the preferred embodiments of the invention have been described. It should be understood that the invention is not limited to the embodiments disclosed, but is intended to embrace any alternative, modifications, rearrangements, or substitutes of parts or elements as fall within the spirit and scope of the invention.

I claim:

1. A support belt comprising:
   an inner elastic belt for providing support to a wearer while flexing with and conforming to the wearer throughout a wide range of movement;
   an outer inelastic belt for providing substantially unyielding support to the wearer;
   the inner and outer belts sized for completely encircling the lower lumbar and abdominal regions of a wearer;
   the inner and outer belts including fastening means securing the ends of each belt together;
   at least one flexible supplemental support means secured to the inner belt, for flexing at room temperature to conform to the sides of a wearer throughout a wide range of natural movement and positioned for provision of increased support to a predetermined portion of the lower lumbar region of the wearer;
   a portion of said inelastic outer belt adjacent the supplemental support means having a width substantially less than said inner belt and said flexible support means, to avoid restricting concave and convex elastic flexure of those portions of the inner elastic belt and the flexible support means extending beyond the more narrow outer belt, as the wearer moves throughout a wide range of movement; and
   said elastic inner belt having sufficient elastic strength to continuously conform the inner belt and the supplemental support means convexly and concavely to the shape of the wearer, providing support without restricting the range of motion of the wearer.

2. A support belt of claim 1 wherein the inner belt is of relatively uniform width and thickness along its length.

3. A support belt of claim 1 wherein the outer belt is of uniform width and thickness along its length.

4. A support belt of claim 1 wherein the fastening means of the inner belt includes Velcro ® fasteners at both of its ends.

5. A support belt of claim 1 wherein the fastening means of the outer belt includes:
   Velcro ® fasteners located at one end of the outer belt; and
   a ring secured to the opposite end of the outer belt.

6. A support belt of claim 1 wherein the non-removable, flexible supplemental support means of the inner belt includes a support pad secured within a middle panel for increased support to the lower lumbar region of an individual.

7. A support belt comprising:

an inner, elastic belt for completely encircling the lower lumbar and abdominal regions of an individual;

an outer, inelastic belt for completely encircling the lower lumbar and abdominal regions of an individual wherein the outer belt overlies the inner belt;

said inner and outer belts having fastening means at each of their ends;

said inner belt containing at least one non-removable, flexible supplemental support means within a middle panel, for flexing at room temperature to conform to the sides of a wearer throughout a wide range of natural movement;

at least one of said non-removable, flexible supplemental support means including padding secured within the middle panel for protecting the lower lumbar region of the back;

said inner belt including a flexible side panel on either side of the middle panel;

said side panels including flexible padding for providing increased support along the oblique regions of an individual;

said outer belt being of substantially less width than said inner belt to avoid restricting concave and convex elastic flexure of said inner belt, support means and side panels as the wearer moves throughout a wide range of positions;

said elastic inner belt being elastic in both the horizontal and vertical directions; and said inner and outer belts having sufficient elastic strength to deform the supplemental support means and the oblique support padding to the shape of an individual without restricting the range of motion of the individual.

8. A support belt of claim 1 further comprising oblique support means for the oblique regions including:

a side panel located on either side of the one or more of the flexible support means of the inner belt for the placement of supplemental padding; and padding secured within each side panel for increased support of the oblique muscle groups of an individual.

9. A support belt of claim 1 wherein the relatively elastic inner belt remains elastic in both the horizontal and vertical directions during use.

10. The support belt of claim 1 wherein the relatively elastic inner belt is elastic in both the horizontal and vertical directions.

11. A support belt of claim 1 wherein the outer belt is secured to the inner belt at a plurality of spaced locations, across only a portion of the width of the inner belt, to allow elastic stretching and contraction of the inner belt adjacent its longitudinal edges.

12. The support belt of claim 7 wherein the outer belt is secured to the inner belt at a plurality of spaced locations, across only a portion of the width of the inner belt, to allow elastic stretching and contraction of the inner belt adjacent its longitudinal edges.

* * * * *